United States Patent [19]

Pannwitz

[11] Patent Number: 4,848,166
[45] Date of Patent: Jul. 18, 1989

[54] WEARABLE AIR SAMPLING DEVICE

[75] Inventor: Karl-Heinz Pannwitz, Lübeck, Fed. Rep. of Germany

[73] Assignee: Draegerwerk AG, Fed. Rep. of Germany

[21] Appl. No.: 199,327

[22] Filed: May 26, 1988

[30] Foreign Application Priority Data

May 26, 1987 [DE] Fed. Rep. of Germany ....... 8707573

[51] Int. Cl.⁴ .................. G01N 1/24; G01N 21/77; G01N 31/22; G01N 1/22
[52] U.S. Cl. .................. 73/864.73; 422/58; 422/86; 351/158; 73/863.31; 73/864.34
[58] Field of Search ............ 73/864.34, 864.73, 864, 73/863.31, 863.21; 422/58, 59, 60, 86, 104; 351/158

[56] References Cited

U.S. PATENT DOCUMENTS

| | | | |
|---|---|---|---|
| 2,168,705 | 8/1939 | Fransisco et al. | 128/206 |
| 3,286,506 | 11/1966 | Lloyd | 422/86 X |
| 3,378,348 | 4/1968 | McConnaughey | 422/60 |
| 3,847,552 | 11/1974 | Hobgood et al. | 422/86 X |
| 4,589,292 | 5/1986 | Delhaye et al. | 73/863.03 |

FOREIGN PATENT DOCUMENTS

| | | |
|---|---|---|
| 7041556 | 5/1971 | Fed. Rep. of Germany . |
| 2233660 | 1/1974 | Fed. Rep. of Germany . |
| 2505089 | 10/1980 | Fed. Rep. of Germany . |
| 3215466 | 11/1983 | Fed. Rep. of Germany . |
| 3321356 | 12/1984 | Fed. Rep. of Germany . |
| 3137756 | 12/1986 | Fed. Rep. of Germany . |
| 367529 | 2/1932 | United Kingdom ........ 422/104 |
| 2037982 | 7/1980 | United Kingdom ........ 422/60 |
| 2165355 | 4/1986 | United Kingdom ........ 422/86 |

Primary Examiner—Tom Noland
Attorney, Agent, or Firm—McGlew & Tuttle

[57] ABSTRACT

A wearable, air-sampling device includes a head frame comparable to an eyeglass head frame which has a forehead engaging cross piece and an ear-engaging piece on each side extending rearwardly from the forehead engaging portion which are adapted to engage over respective ears of the wearer and which includes a detachable gas-tester holder mounted on the frame at some visible location, for example, between the eye portions of the forehead piece or over each eye of even on a temple piece.

10 Claims, 2 Drawing Sheets

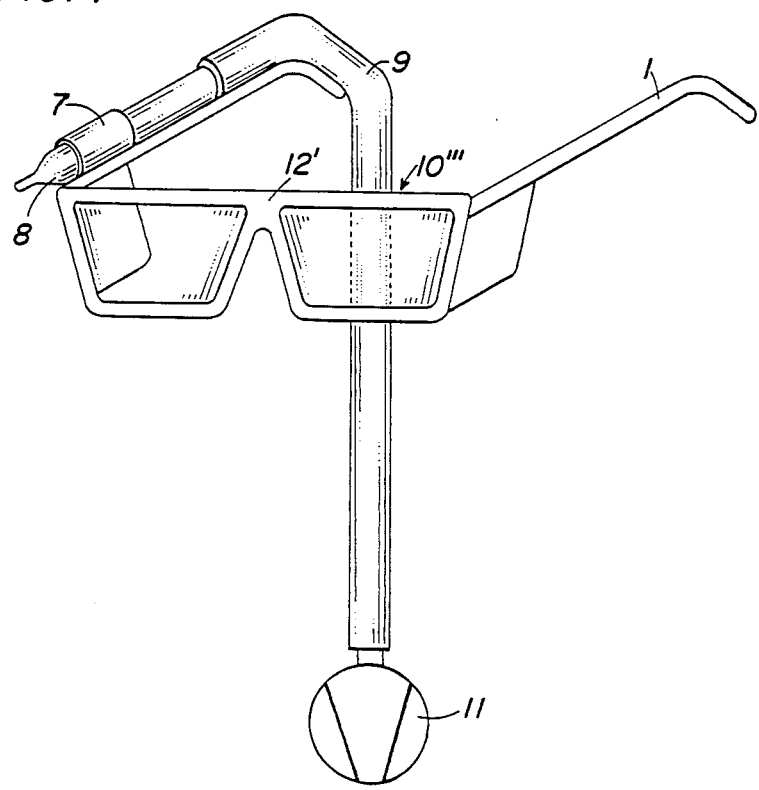

WEARABLE AIR SAMPLING DEVICE

BACKGROUND OF THE INVENTION

1. Field of the Invention

The invention relates, in general, to gas testing and sampling devices and, in particular, to a new and useful device for holding a passive or active sampling unit for taking air samples in a person's inhalation region.

In personal air monitoring, the air samples should be taken in the inhalation region.

There is a familiar arrangement of a sampling unit, which can be secured by a clip to the lapel of a suit or to the outer breast pocket of this garment (German Utility Model No. 70 41 556, as well as German patent No. 31 37 756 and German publication No. 33 21 356).

The placement of a sampling unit in the protective helmet of the person being protected and, thus, very close to the air measurement site of actual interest, is mentioned in German Patent No. 25 05 089. A spectacle frame holding element for securing of nose probes is desired, for example by U.S. Pat. No. 2,168,705 and German patent No. 32 15 466.

The arrangement of a test tube-shaped sampling unit in a holder on a protective helmet, with a suction opening lying in the region of the mouth of the wearer, is known from German Patent No. 22 33 660.

The aforementioned designs with the sampling unit arranged on the lapel of a jacket in the upper breast region and with the unit arranged in the protective helmet may produce entirely different concentration relationships than those in the inhalation region, which is the region of true significance for the monitoring.

SUMMARY OF THE INVENTION

The invention provides a device enabling an adequate holding of an active or passive sampling unit in a person's relevant inhalation region, the wearing of which only slightly hampers the wearer.

The holder is fashioned as a spectacle frame holding element and is provided with at least one detachable holding section for the sampling unit. The sampling unit can be configured either as a one-end open diffusion test tube, or (and preferably) as a double-ended open tube with two-side diffusion layer. Another more effective possibility is to fashion the sampling unit as forced-flushing test tube of a gas detector with air suction.

In a preferred configuration, a holding section for the sampling unit is arranged on a cross bridge of the holding element in the nose area thereof. Another possibly advantageous configuration provides two holders in symmetrical arrangement on the cross bridge of the holding element. Finally, it may be profitable to arrange a holder for the sampling unit on at least one side frame of the holding element.

Accordingly, it is an object of the invention to provide a wearable air-sampling device which comprises a head frame which has a forehead engaging cross piece and an ear-engaging piece on each side of the forehead engaging piece and with a detachable gas tester holder mounted on the frame.

A further feature of the invention is to provide with a frame with a detachable gas tester holder thereon which is simple in design, rugged in construction and economical to manufacture.

The various features of novelty which characterize the invention are pointed out with particularity in the claims annexed to and forming a part of this disclosure.

For a better understanding of the invention, its operating advantages and specific objects obtained by its uses, reference is made to the accompanying drawings and descriptive matter in which preferred embodiments of the invention are illustrated.

BRIEF DESCRIPTION OF THE DRAWINGS

In the drawings:

FIG. 4 is a perspective view of a holder as a spectacle frame with an active sampling unit arranged on a side frame.

GENERAL DESCRIPTION OF THE PREFERRED EMBODIMENTS

Figure 1:
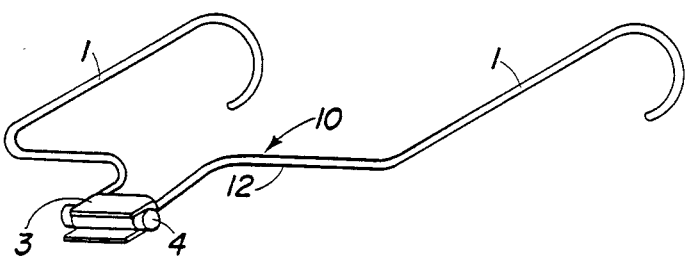
FIG. 1 is a perspective view of a spectacle frame holder with passive sampling unit.

Referring to the drawings, in particular, the invention embodied therein comprises a head frame generally designated 10 which has a forehead engaging cross piece 12 and an ear-engaging piece 1 on each side of the forehead-engaging cross piece which extend rearwardly for engagement with respective ones of the wearer's ears. In accordance with the invention, a detachable gas tester holder 3 for a testing tube 4 is detachably mounted on the frame 10.

FIG. 1 shows the frame holding element 10, which is provided with a holder 3 fashioned as a spring clamp for replaceable holding of a double-ended open diffusion test tube 4 on a front cross bridge or forehead engaging portion 12. The frame 10 includes ear-engaging side piece 1.

Figure 2:
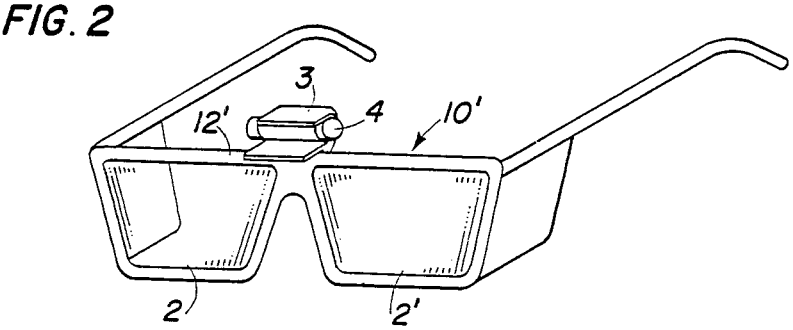
FIG. 2 is a perspective view of a holder as a spectacle frame with sampling unit arranged in the nose region.
Figure 3:
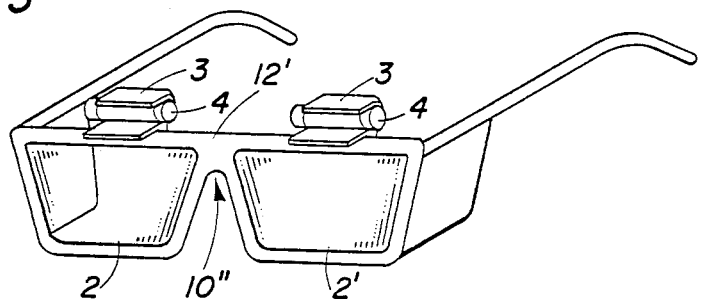
FIG. 3 is a perspective view of a holder as a spectacle frame with two symmetrically arranged passive sampling units.

The examples of FIGS. 2 and 3 concern spectacle frames 10' and 10'', which in the example of FIG. 2 carry a holder 3 for the test tube 4 in a symmetrical central position on the cross bridge 12' centrally of eyepieces 2 and 2' and also over each eyepiece 2 and 2'. In the example of FIG. 3, there are two diffusion test tubes 4 in two holders 3, symmetrically arranged on the cross bridge 12'.

Finally, FIG. 4 also shows a holder 10''' as a spectacle frame, in which a holder 7 for an active test tube 8, in the form of a spring clip, is arranged on a side frame. The suction end of this test tube 8 is connected to a suction pump 11 by hose lines 9.

While specific embodiments of the invention have been shown and described in detail to illustrate the application of the principles of the invention, it will be understood that the invention may be embodied otherwise without departing from such principles.

What is claimed is:

1. A wearable air-sampling device comprising an eyeglass frame having a front portion with opposite sides spaced-apart, lenses and a central nose piece and having a side piece connected to each side of said front portion with ends having ear-engagement portions, a holder clamp mounted on said eyeglass frame, an air-sampling unit held by said holder clamp, the air sampling unit having respective ends projecting outwardly from opposite sides of the clamp, the ends of the air sampling unit being opened for the passage of a gas therethrough.

2. A wearable air-sampling device according to claim 1, wherein there is a holder mounted over each lens, each holder having a gas tube therein having opposite opened ends and including a filling in at least one said tube located adjacent each opening thereof providing two different materials which are reactive with gases.

3. A wearable air sampling device, comprising a head frame having a forehead-engaging cross piece and an ear-engaging piece on each side of said cross piece extending rearwardly therefrom for engaging respective ears of a wearer, and a holder mounted on said frame, said holder detachably holding a gas tester element, said holder comprising a clamp having clamping arm portions which are spaced apart and clamp said gas tester element therebetween so as to leave said test element visible for ease in inspection thereof.

4. An air sampling device according to claim 3, wherein said holder is mounted on said cross piece centrally between opposite ends of said cross piece in a position overlying a nose of the wearer.

5. An air sampling device according to claim 3, wherein said head frame comprises an air eyeglass frame including a pair of spaced apart lenses held by said cross piece, said holder being mounted centrally between the lenses on said cross piece.

6. A wearable air sampling device according to claim 3, wherein said holder is mounted on at least one ear-engaging piece.

7. A wearable air sampling device according to claim 3, wherein said gas tester element comprises a double-ended open gas testing tube having a detectable substance therein arranged adjacent each end.

8. A wearable air sampling device according to claim 3, wherein the gas tester element comprises a gas testing tube held in said holder, said tube having opposite open ends, the sampling device also including means for pumping gases through said tube connected to at least one of the open ends of the tube.

9. A wearable air-sampling device according to claim 8, wherein said holder is mounted on one ear-engaging piece, said gas testing tube having one open end mounted in said holder extending forwardly thereof, the opposite end of the tube being a rear end, the sampling device also including a pump having a hose connection to the opposite rear end of the tube.

10. A wearable air sampling device, comprising a head frame having a forehead-engaging cross piece and an ear-engaging piece on each side of said cross piece extending rearwardly therefrom for engaging respective ears of a wearer, said head frame comprising an eyeglass frame, said cross piece having central nose-engaging portions with a lens on each side thereof and including a holder mounted on said cross piece over each of the eyeglass lenses, each respective one of the holders detachably holding a respective gas tester element.

* * * * *